United States Patent
Secrest et al.

(10) Patent No.: US 6,814,739 B2
(45) Date of Patent: Nov. 9, 2004

(54) RETRIEVAL DEVICE

(75) Inventors: Dean J. Secrest, Concord, OH (US); Marlin E. Younker, West Palm Beach, FL (US)

(73) Assignee: U.S. Endoscopy Group, Inc., Mentor, OH (US)

( * ) Notice: Subject to any disclaimer, the term of this patent is extended or adjusted under 35 U.S.C. 154(b) by 99 days.

(21) Appl. No.: 10/146,273

(22) Filed: May 15, 2002

(65) Prior Publication Data

US 2003/0004538 A1 Jan. 2, 2003

Related U.S. Application Data

(60) Provisional application No. 60/292,168, filed on May 18, 2001.

(51) Int. Cl.[7] .............................................. A61B 17/24
(52) U.S. Cl. ...................... 606/114; 606/113; 606/200
(58) Field of Search ........................ 606/113–114, 117, 606/127, 200

(56) References Cited

U.S. PATENT DOCUMENTS

| | | | | | |
|---|---|---|---|---|---|
| 5,643,283 | A | * | 7/1997 | Younker | 606/17 |
| 5,759,187 | A | * | 6/1998 | Nakao et al. | 606/114 |
| 5,906,621 | A | * | 5/1999 | Secrest et al. | 606/114 |
| 6,093,195 | A | * | 7/2000 | Ouchi | 606/113 |
| 6,235,026 | B1 | * | 5/2001 | Smith | 606/46 |

* cited by examiner

*Primary Examiner*—(Jackie) Tan-Uyen T. Ho
(74) *Attorney, Agent, or Firm*—Watts Hoffmann Co.

(57) ABSTRACT

An endoscopic surgical device for retrieving severed tissue or foreign bodies from within a subject is disclosed. The device comprises a support unit and a tissue retrieving net system. The net system is carried by the support unit and may be inserted into the subject through an orifice or small incision and operated to retrieve tissue that has been severed by a conventional method. The net system comprises a net, a net actuator, a net deployment and retrieval assembly for transmitting motion between the net and its actuator. The net system further comprises at least one net connector disposed such that only one connector is within an articulation zone, defined by locations of severe bending of the device during operation.

2 Claims, 3 Drawing Sheets

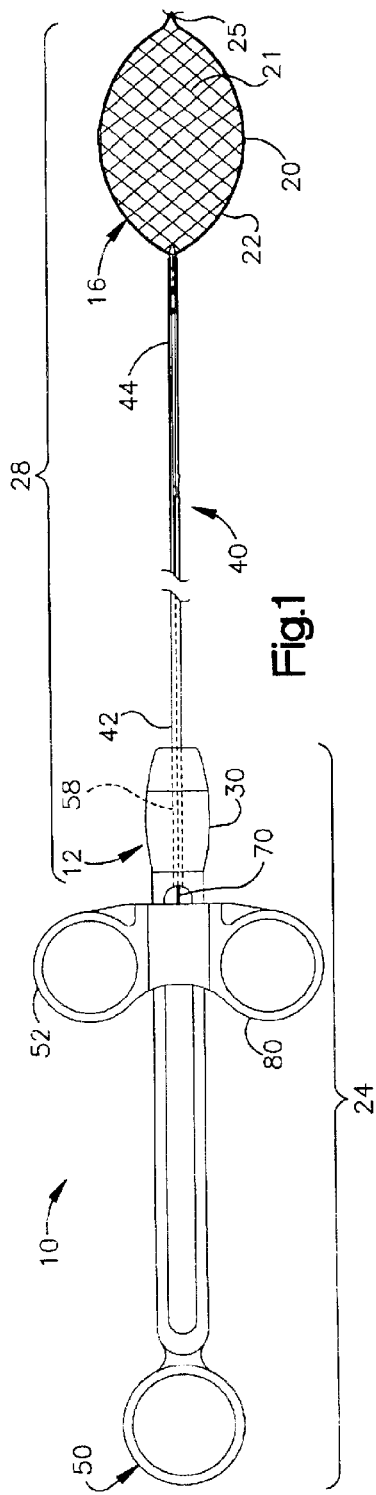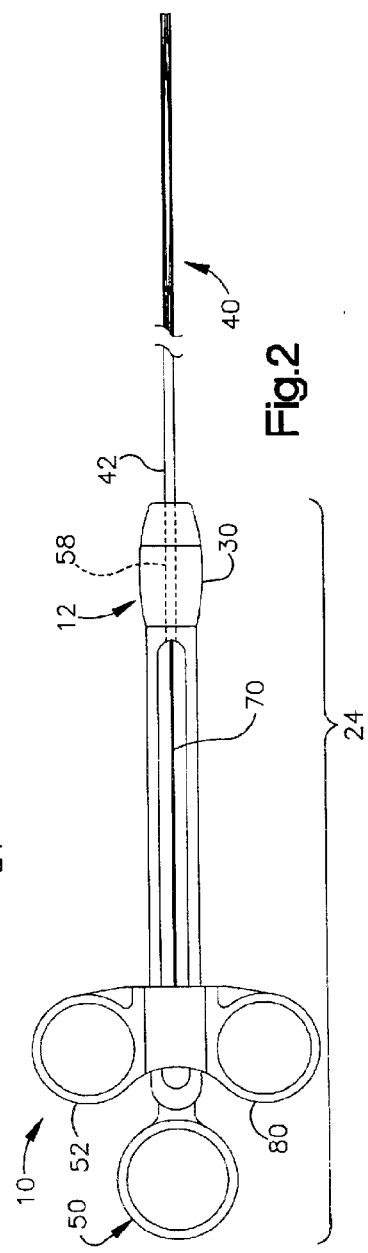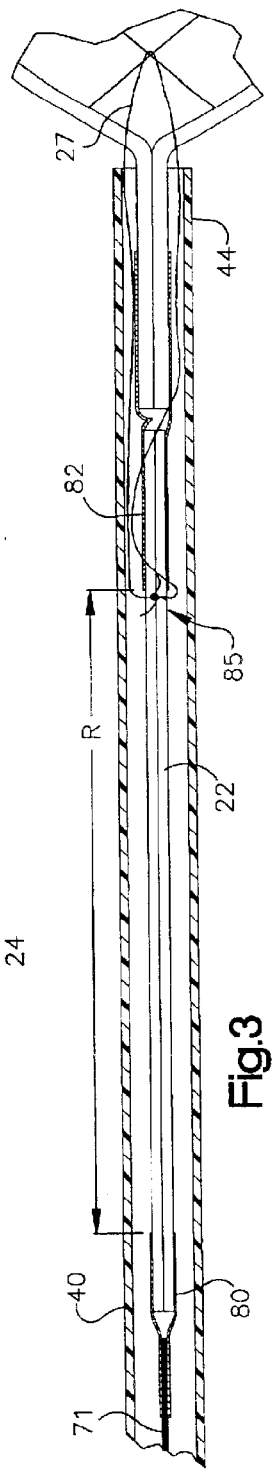

RETRIEVAL DEVICE

CROSS-REFERENCE TO RELATED APPLICATIONS

This non-provisional application claims benefit of U.S. Patent Provisional Application Ser. No. 60/292,168, entitled "Retrieval Device," filed on May 18, 2001.

FIELD OF THE INVENTION

The present invention relates to surgical devices and more particularly to endoscopic retrieval devices constructed for retrieving relatively small pieces of sample tissue or foreign bodies from a human subject through orifices or small incisions.

BACKGROUND OF THE INVENTION

Snares, baskets, and graspers are in widespread use for severing capturing and retrieving tissue specimens and foreign bodies from within subjects. The devices are used in human and animal subjects, in laparoscopic surgeries and other procedures where access within a subject is only possible via a small opening. One exemplary use is for cutting off and retrieving intestinal polyps where a wire snare, passed through an colonoscope instrument channel, encircles and is tightened about an intestinal polyp to sever the polyp. The severed polyp is retrieved in a net inserted through the instrument channel. The net is manipulated to enclose the polyp and then withdrawn with the instrument so that the tissue architecture remains undisturbed.

In this procedure, as well as others, the net and snare must be quite compact in order to pass into the subject through the instrument channel, or other passage. Prior art proposals have employed snares supported within plastic tubes that were snaked into the subject to locate the snare where desired. The snare was then deployed from its tube, manipulated to cut off the polyp and retrieved into the tube for removal from the subject.

A net, collapsed within another tube, was introduced through the instrument channel, etc., for removing the polyp. When near a target polyp, the net was deployed, like the snare, and manipulated to net the polyp. The net was then closed sufficiently to secure the polyp and withdrawn from the subject.

U.S. Pat. No. 5,643,283 to Younker, which is incorporated herein by reference in its entirety, discloses a device for retrieving an object from within a subject. The device comprises a shaft and a compressible pouch for receiving the object positioned adjacent a distal end of the shaft. The pouch includes a mouth which can be opened and closed. The pouch is retained, in proximity to the distal end of the shaft, on a cable loop by a slidable tether. The net is free to slide on the cable loop to form a pouch at the distal end of the shaft. The tether is fixed at a second location near the proximal end of the shaft, and in one embodiment, is tied off to a ring and secured with heat shrink tubing. When the targeted foreign object is within the pouch, a clinician disengages the ring portion of the handle to close the net around the object. The clinician then removes the device from the patient and unloads the object from the net. The clinician then places the ring on a post, in order to pack the pouch into the distal end of the shaft.

In operation of a commercial embodiment of U.S. Pat. No. 5,643,283, several problematic issues have surfaced. Clinicians have experienced difficulty in understanding the operation of the tether, in particular, the interaction of the ring and post. The ring is to be used to pull the net inside the shaft only when an object is not within the net. In preparation to capture an object, the ring should be disengaged to release the net. The net is then slid over the targeted object and the net is closed. At this point, proper operation would involve merely removing the device from the patient. However, some clinicians when operating the device try to further pull the net inside the shaft when the net is bundled up at distal end of cable loop. This will cause the net to jam, or in some cases, damages the tubing. The occasional improper operation of the device sometimes causes permanent malfunction.

The commercial embodiment discussed above also adds undesirable expense to the product. Specifically, the full length tether and heat shrink operation add material cost and labor assembly cost to the device.

The present invention provides a new and improved retrieval device that is so constructed and arranged that net movement during deployment and retrieval is not prohibitively restricted. Secure net attachment is assured and that provides for convenient net packing in the introducer passage. The device provides a convenient and economical method of sample retrieval during endoscopic procedures. The new retrieval device is easy assemble, manufactured at a reduced cost, and easier to use by the end consumer.

SUMMARY OF THE INVENTION

In one illustrated embodiment of the present invention an endoscopic surgical device for retrieving severed tissue from within a human subject is provided. The device includes a support unit and a tissue retrieving net system.

The support unit includes a body and an elongated introducer member. The body defines a first passage therethrough. The introducer has a first end section proximal and fixed with respect to the body and a second end section remote from the body. The introducer member further defines a second passage aligned with the first passage and opening at the second end section.

The tissue retrieving net system includes a net, a net deployment and retrieval assembly and a net actuator system.

The net includes a wire-like resilient loop and a net element having a mouth section slidably disposed on the loop and a tissue receiving pouch section. The loop terminates with two relatively parallel loop cables. The net is disposed adjacent the second end for deployment and retraction through the second passage opening.

The net deployment and retrieval assembly extends substantially through the first and second passages and connects to the net. The assembly further includes a motion transmitting member extending in the second passage to the loop.

The net actuator unit includes a first handle fixed with respect to the body and a second handle fixed with respect to the motion transmitting member and movable relative to the first handle. The act of shifting the second handle relative to the first handle shifts the net into and out of the second passage opening.

The introducer member second passage has a diameter substantially smaller than the width of the loop as deployed. The member engages the loop at the second end section opening and resiliently collapses and elongates the loop as the net is retracted and moves into the introducer member passage. The loop resiliently returns to its uncollapsed configuration as it is deployed.

In one embodiment, the net system includes at least one connector adapted to fasten each loop cable. The ends of the net element are secured to the motion transmitting member on the proximal side of the at least one connector with respect to the support unit.

In a second embodiment, the net system further includes a first connector, a second net connector proximal to the second passage opening, and an intermediate portion defined by an axial space on the loop cables between the first connector and the second connector. The first connector and the second connector are adapted to fasten each loop cable. Ends of the net element are secured to the loop within the intermediate loop portion between the first connector and the second connector.

The deployment and retrieval assembly may include a thin, flexible wire-like motion transmitting member between the net actuator unit and the loop. The motion transmitting member extends within an introducer guide passage which closely surrounds the motion transmitting member and constrains the member for translational longitudinal motion within the passage.

The first connector may be disposed at least 6 inches from the second connector, such that only one connector is within an articulation zone during deployment of the net element.

The ends of the net element may be secured to the motion transmitting member adjacent a proximal shoulder of the connector with respect to the support unit.

The present invention offers advantages over devices available in the prior art. In a second embodiment, the net is fixed distally and proximally by the use of a first and second connector. The connectors are sufficiently spaced apart to provide secure net attachment without the use of additional tether mechanisms. The connectors are positioned such that only one may be within an articulation zone of the endoscope at a time, permitting ease of net deployment in a variety of geometric operating configurations.

In a first embodiment, only one connector is used to secure the proximal side of the net. This technique decreases the amount of cable loop length within the articulation zone. The reduction in cable loop length effectively reduces the amount of rigid material within the articulation zone of the endoscope at a time, further permitting ease of net deployment in a variety of geometric operating configurations.

The device is also easier to assemble and less expensive to manufacture than certain conventional designs.

Further features and advantages of the invention will become apparent from the following detailed description made with reference to the accompanying drawings.

BRIEF DESCRIPTION OF THE DRAWINGS

FIG. 1 is an elevational view of a surgical device constructed according to one embodiment of the present invention, illustrated with the net element deployed;

FIG. 2 is a view similar to FIG. 1, illustrated with the net element retracted;

FIG. 3 is an enlarged fragmentary view of a part of the device illustrated in FIG. 1, showing detail of the introducer member;

BEST MODE CONTEMPLATED FOR CARRYING OUT THE INVENTION

Figure 4:
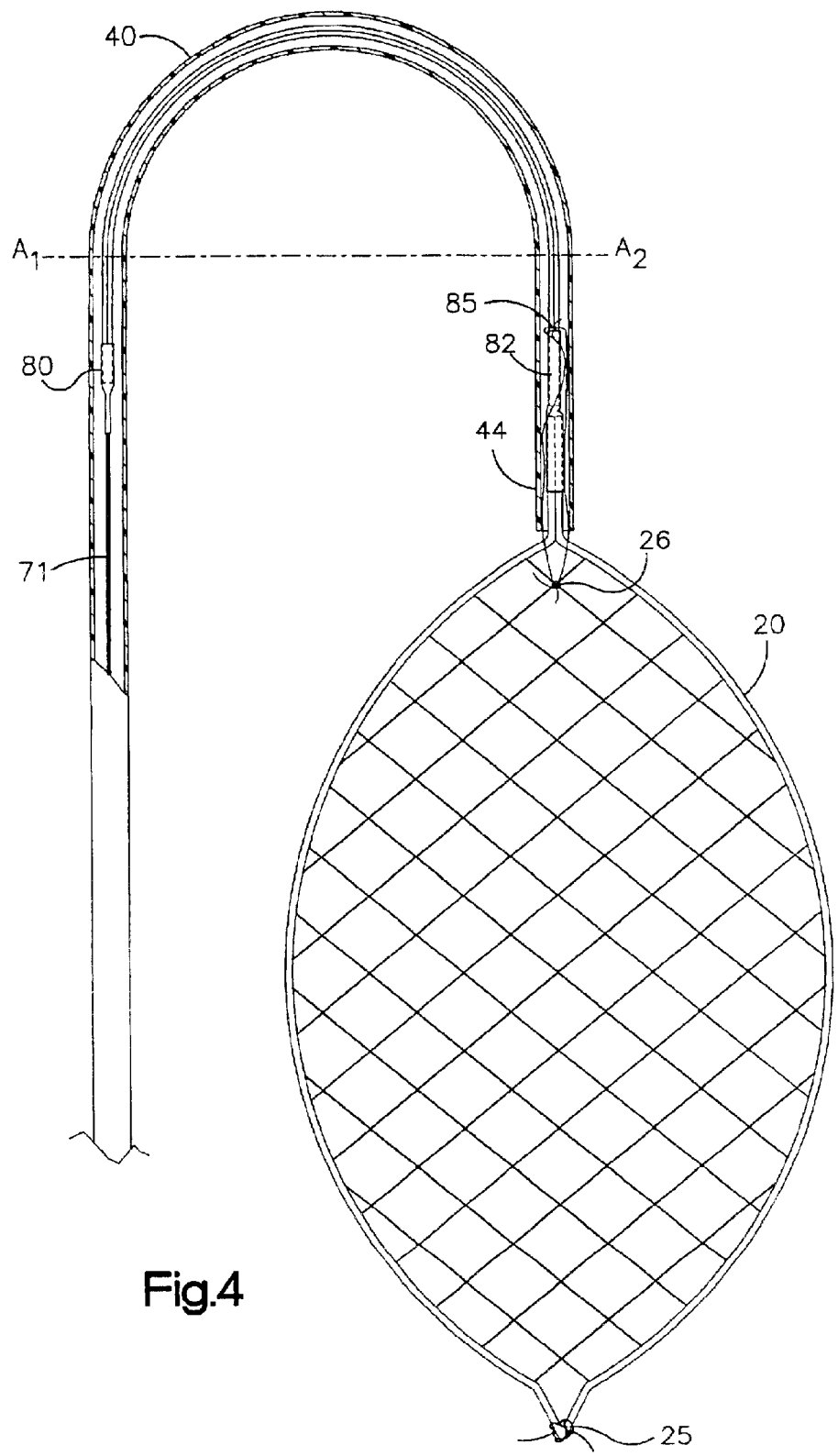
FIG. 4 is an enlarged fragmentary view of part of the device illustrated in FIG. 1, with the device show as positioned in a sample configuration within a subject.

An endoscopic surgical device 10 for retrieving severed tissue and or foreign bodies from within a subject is illustrated by the drawings. Referring to FIGS. 1 and 2, in one embodiment, the device 10 comprises a support unit 12 and a tissue retrieving net system 16. The net system is carried by the unit 12 and is so constructed and arranged that it may be inserted into the subject through an orifice or small incision and operated to retrieve a tissue sample previously detached from the subject by a conventional method, e.g., a snare/cautery system. Accordingly, the net system 16 comprises a net 20, a net actuator 24, and a net deployment and retrieval assembly. 28 for transmitting motion between the net and its actuator 24. The net 20 comprises a net element 21 and a net loop 22 and a distal 25 and proximal 26 tie off suture that secures the net.

The device 10 can be used with any suitable or conventional endoscopic or laparascopic surgical equipment. For purposes of this disclosure the device 10 is described in the context of use with an endoscope/colonoscope/sigmoidoscope type apparatus (not illustrated), of conventional or suitable construction. The scope is provided with an elongated body having a controllably flexible projecting end region. Surgical instruments, such as the device 10, may be introduced through an instrument channel, which extends through the scope body, for retrieving tissue targeted by the surgeon manipulating the scope.

The support unit 12 supports the net system 16 so that the net 20 can be inserted through the scope instrument channel by a surgeon. The support unit 12 comprises a body 30 defining a passage and an elongated introducer 40 having a first end section 42 proximal and fixed with respect to the body 20 and a second end section 44 remote from the body. The introducer 40 is tubular and aligned with the body passage for receiving the net system.

The illustrated introducer 40 is a smooth, supple member capable of being snaked through the scope instrument channel into the subject and readily flexed into any shape required as the scope body is flexed by the surgeon. In the illustrated embodiment, the introducer 40 is a generally cylindrical, small diameter tube formed of non-reactive low friction plastic material, such as polytetrafluouroethylene. The first end section 42 is fixed to the body 30 while the second end section 44 houses the net for individual deployment and retrieval.

The net actuator 24 is adapted for reciprocating the deployment and retrieval assembly in the body and introducer to operate the net 20. The actuator 24 comprises a first handle 50 fixed with respect to the body 30 and a second handle 52 attached to the deployment and retrieval assembly 28 and movable with respect to the handle 50.

The second handle 52 is fixed to the assembly 28 and mounted on the handle 50 between its ends for longitudinal sliding movement. The second handle comprises a dual finger ring member 80 slidable on the handle 50. The handles 50, 52 as illustrated are formed from molded plastic materials.

The deployment and retrieval assembly 28 is constructed and arranged to transmit considerable deployment and retractive forces to the net while enabling the scope body to be freely manipulated and flexed to position the net where desired. The assembly 28 comprises a link comprises a first link section 70 and a second link section 71 connected to the actuator 24 for transmitting compressive and tensile forces between the handle 52 and a bore 58. The bore 58 is disposed within the center of the body 30. The link 70 transmits relatively substantial compressive forces without bending or breaking. The illustrated first link section 70 is formed from hypodermic needle stock, i.e., it is a cylindrical stainless steel tube. The second link section 71 as illustrated is a multi-strand cable. The first link section 70 joins the second link section 71 as the link exits the body 30.

The link 71 extends from the body 30 and within the introducer 40 so that it must flex with the introducer yet transmit compressive and tensile forces. The illustrated link 71 is closely surrounded by the body passage of the introducer passage 40. The link 71 is relatively stiff compared to the supple introducer. When transmitting compressive forces, the link 71 is resiliently deformed to bow against the introducer wall. The link 71 has good compressive and tensile strength and is somewhat resiliently bendable. The link 71 will bend appreciably without yielding and kinking.

A first connector 80 and a second connector 82 fix the loop 22 in two locations with respect to the net 20. The proximal side of the net is tied off at a location 85 between the loop cables. As illustrated in FIG. 3, a tether 27 is used to tie off the proximal side of the net. This tether is shorter than conventional tethers that travel the full length of the introducer. No further tethering system is required, although additional net mounting techniques may be employed in the practice of the invention.

Referring now to FIG. 3, the first connector 80 joins the link 71 and the loop 22 together structurally. The illustrated connector 80 is a short tube crimped to both ends of the loop 22 and to the second link section 71, The illustrated connector tube is crimped about the loop and link to form a cross sectional shape, which is capable of rotating within the introducer 40. The illustrated connector 80 is formed from hypodermic needle stock, like the first link section 70. The second connector 82 further joins opposing portions on the net loop 22 at a location proximal to the net 20 with respect to the first connector 80.

In the illustrated embodiment, the space between the two loop cables is utilized to fix the net element 21 with respect to the link 71. An intermediate region R, shown in FIG. 3, axially between the first connector 80 and the second connector 82 within the introducer 40 may be used. In an exemplary embodiment, the proximal side of the net element 21 with respect to the support system 12 is fixed to the net loops 22 at a convenient location 85. Suture material, or another known suitable method, may be used to tie the net to the loop.

The net 20 is deployed from the introducer second end 44 and manipulated by the surgeon to net severed tissue and secure the tissue for retrieval from the subject. The net 20 may be deployed after a snare or similar technique has severed the target tissue. The net 20 comprises a pouch-like net element 21 slidably supported on the loop 22.

The illustrated net loop 22 is formed from a loop of fine wire constructed and arranged to cooperate with the introducer to deploy and retract the net 20. The illustrated loop 22 is a stiff, resilient flexible wire having its respective ends crimped in place in two locations by the first and second connector 80, 82. When the net is deployed from the end of the introducer, the loop resiliently expands to a relaxed condition where the loop width is substantially greater than the introducer diameter. The deployed snare is guided to a position where it receives a target polyp or other tissue. The net is retracted by the surgeon. As the net is retracted into the introducer second end 44 the loop resiliently bears against the introducer wall so the loop resiliently collapses, narrowing the loop portion projecting from the introducer. Tissue or another object captured within the net element 21 is progressively constricted by the elastic nature of the net, allowing for a wide range of sized objects to fit inside the net without compromising the architecture preservation or the security of the object, as the net is being drawn toward the distal end of the introducer.

The net element 21 is an extremely light pouch-like structure having the net loop wire extending through the mesh about its periphery to form a net mouth slidably supported on the loop and a depending pouch. The net fibers are quite fine, yet sufficiently strong that the net element may slide along the loop wire in the direction away from the connectors 80, 82 to enclose tissue within the pouch as the net is retrieved and/or to gather the entire net at the distal net loop end when the net loop has been retrieved. The net has minimal bulk so that when an empty net is retrieved, it easily moves completely into the introducer passage.

The illustrated net is formed from 100% nylon fibers having strand diameters of from about 0.0125 mm–0.04 mm. The fibers are woven in a diamond mesh pattern with the mesh strands spaced from 1 mm–3 mm and their intersections fixedly secured together. The illustrated netting material is substantially like that of a fine mesh hair net. The net is formed by cutting about a square, circular or elliptical section of the net, trimming or otherwise finishing the edges and threading the loop wire through the peripheral mesh elements. The cut net section size is selected sufficiently larger than the net loop area to assure that a pouch-like, tissue receiving portion suspends from the net mouth, but not too large to create undesirable bulk and difficulty packing the net when pulling it inside the shaft.

Attempting to fully retrieve a tissue containing net into the introducer 40 can result in tissue loss by forcing the tissue through the net. The net fibers are fine and strong so they may cut the tissue or they may be broken, either of which alternative is undesirable. A net actuator thumb ring may be provided with a tag (not illustrated) warning the surgeon not to continue retrieving the net against unusual resistance.

The present invention resolves problems faced by surgeons and nurses working with some prior art designs. Nurses and doctors have experienced difficulty in understanding the operation of the tether, specifically the interaction of the ring and post. Therefore, occasionally the device is operated incorrectly causing malfunction. The present design allows a nurse to pull back on the handle to conveniently pack the net inside the introducer passage.

Further, often a surgeon is required to manipulate the endoscope into difficult to access internal areas. Certain procedures require bending or twisting the endoscope. The area of the endoscope that is twisted or bent is called the articulation zone.

Some net devices have featured multiple connector designs in which the connectors are spaced somewhat adjacently with the second end section 44. In these designs, the multiple connectors on the net devices have resisted bending of the scope. Moreover, the friction created has made deployment of the net difficult once the scope has been desirably positioned by the surgeon. One advantage of the present invention is increased freedom of movement, and ease of net deployment, within the articulation zone.

During operation of the system 10, the surgeon experiences an increased ease of use over prior art designs. In the illustrated embodiment, the first connector 80 is axially disposed a distance from the second connector 82, such that only one connector is within the articulation zone (bounded by $A_1, A_2$), defined along the introducer 40 longitudinal axis, during deployment of the net element. In the illustrated system, the first connector 80 is disposed at least six inches from the second connector 82.

The articulation zone defines the axial portion of the introducer 40 within a substantially non-linear position. The articulation zone typically includes bends of greater than 30° and can exceed 200° at a radius of 0.75 inches or less.

Referring to FIG. 4, a portion of the system 10 is illustrated as positioned in a probable configuration within a subject. During operation of the scope, a surgeon may manipulate the second end section 44 of the introducer into a severe articulated position. At times, the second end section may be bent up to 180°, as illustrated in FIG. 4. Deployment of the net 20 in this and similar positions is difficult when the connectors 80, 82 are both within the articulation zone. The combined kinetic frictional force of each connector against the inside of the introducer passage would otherwise make deployment of the net difficult. As illustrated in FIG. 4, the surgeon more easily deploys the net in a variety of positions.

Figure 5:
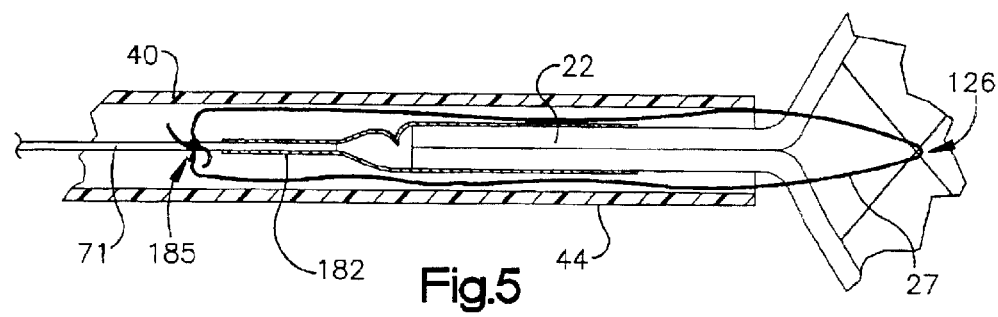
FIG. 5 is an enlarged fragmentary view of part of a surgical device constructed according to a second embodiment of the present invention, showing detail of the introducer member.
Figure 6:
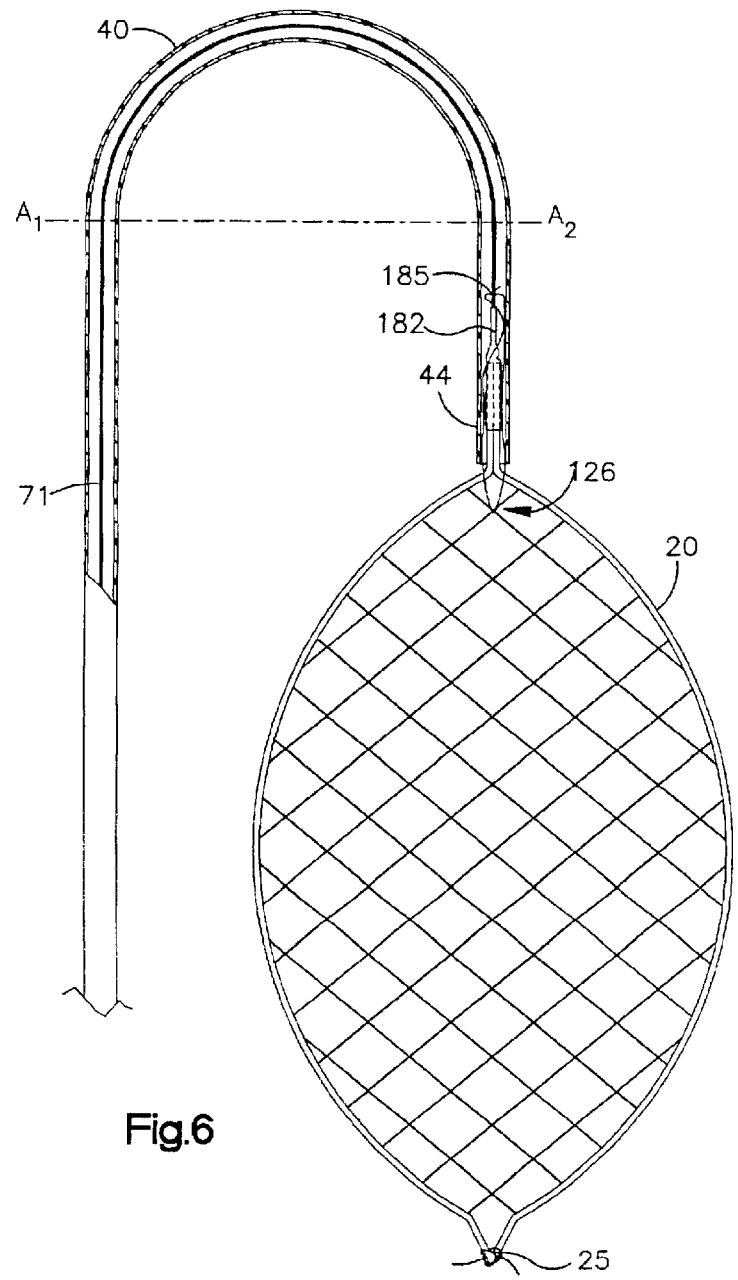
FIG. 6 is a enlarged fragmentary view of part of the device illustrated in FIG. 5, with the device show as positioned in a sample configuration within a subject.

A second embodiment of the present invention is illustrated by the drawings. A part of an endoscopic surgical device 10 for retrieving severed tissue and or foreign bodies from within a subject is illustrated in FIGS. 5 and 6. In this illustrated design, the device 10 includes a support unit 12 and net actuator 24 as previously described. However, an alternative construction of a net deployment and retrieval assembly 28 is utilized.

In the illustrated design, the net deployment and retrieval assembly 28 uses a single connector. Referring now to FIG. 5, the connector 182 joins the link 71 and the loop 22 together structurally. The illustrated connector 182 is a short tube crimped to both ends of the loop 22 and to the second link section 71. The illustrated connector tube is crimped about the loop and link to form a cross sectional shape, which is capable of rotating within the introducer 40. The illustrated connector 182 is formed from hypodermic needle stock, like the first link section 70.

One goal of the design is to reduce the amount of rigid material within the articulation zone. During operation of the system 10, the surgeon experiences an increased ease of use over prior art designs. As illustrated in FIG. 6, the length of rigid material within the articulation zone (bounded by $A_1, A_2$), defined along the introducer 40 longitudinal axis, is minimized during operation of the net element. The reduction in rigid material results from reducing the length of loop cable 22 within the articulation zone.

As shown in FIG. 5, the proximal side of the net element 21 with respect to the support system 12 is fixed to the net loops 22 at a convenient location 185. Suture material, or another known suitable method, may be used to tie the net to the loop. As illustrated in FIG. 5, a tether 27 is used to tie off the proximal side of the net. This tether is shorter than conventional tethers that travel the full length of the introducer. The tether 27 may be tied off adjacent the shoulder of the connector 182. As shown, the tether has a diameter not greater than the thickness of the connector shoulder. No further tethering system is required, although additional net mounting techniques may be employed in the practice of the invention.

While two embodiments of the invention has been illustrated and described in considerable detail, the present invention is not to be considered limited to the precise constructions disclosed. Various adaptations, modifications and uses of the invention may occur to those skilled in the arts to which the invention relates. It is the intention to cover all such adaptations, modifications and uses falling within the scope or spirit of the annexed claims.

What is claimed is:

1. An endoscopic surgical device for retrieving severed tissue or foreign bodies from within a human body, the device comprising:
    a. a support unit comprising:
        i. a body having a first passage therethrough, and
        ii. an elongated introducer member having a first end section proximal and fixed with respect to said body and a second end section remote from the body, the introducer member having a second passage aligned with the first passage and opening at said second end section; and
    b. a tissue retrieving net system comprising:
        i. a net comprising a wire-like resilient loop and a net element having a mouth section slidably disposed on the loop and a tissue receiving pouch section, said loop terminating with two relatively parallel loop cables, said net disposed adjacent said second end section for deployment and retraction through said opening;
        ii. a net deployment and retrieval assembly extending substantially through said first and second passages and connected to the net, said assembly comprising a motion transmitting member extending in said second passage to said loop; and
        iii. a net actuator unit comprising a first handle fixed with respect to said body and a second handle fixed with respect to said motion transmitting member and movable relative to said first handle so that shifting the second handle relative to said first handle shifts said net into and out of said opening;
    c. said second passage having a diametrical extent substantially smaller than the width of said loop as deployed, said introducer member engaging said loop at said opening and resiliently collapsing and elongating said loop as said net is retracted and moves into said second passage, said loop resiliently returning to its uncollapsed configuration as it is deployed;
    d. said net system further comprising a connector, wherein the connector secures each loop cable;
    e. wherein with respect to said support unit, a proximal portion of said net element is secured to the motion transmitting member on the proximal side of the connector, and a distal portion of said net element is secured to a center portion of said loop.

2. The device claimed in claim 1 wherein said deployment and retrieval assembly comprises a thin, flexible wire-like motion transmitting member between the net actuator unit and the loop, said motion transmitting member extending within an introducer guide passage, said introducer guide passage closely surrounding said motion transmitting member and constraining said member for translational longitudinal motion within said passage.

\* \* \* \* \*